US009359588B2

United States Patent
Smith

(10) Patent No.: US 9,359,588 B2
(45) Date of Patent: Jun. 7, 2016

(54) MULTILAYERED STRUCTURE INCLUDING CYCLIC OLEFIN POLYMER OR COPOLYMER, AND PHOTOBIOREACTOR INCLUDING THE SAME

(71) Applicant: Raven Industries, Inc., Sioux Falls, SD (US)

(72) Inventor: Daniel S. Smith, Sioux Falls, SD (US)

(73) Assignee: Raven Industries, Inc., Sioux Falls, SD (US)

(*) Notice: Subject to any disclaimer, the term of this patent is extended or adjusted under 35 U.S.C. 154(b) by 62 days.

(21) Appl. No.: 13/713,298

(22) Filed: Dec. 13, 2012

(65) Prior Publication Data

US 2014/0170742 A1    Jun. 19, 2014

(51) Int. Cl.
*B32B 27/00* (2006.01)
*C12M 3/00* (2006.01)
*C12M 1/00* (2006.01)
*B32B 27/08* (2006.01)

(52) U.S. Cl.
CPC ............ *C12M 23/22* (2013.01); *B32B 27/08* (2013.01); *C12M 21/02* (2013.01); *C12M 23/20* (2013.01); *Y10T 428/31913* (2015.04)

(58) Field of Classification Search
CPC ...... C12M 21/02; C12M 31/00; C12M 31/02; C12M 31/08; C12M 31/10
See application file for complete search history.

(56) References Cited

U.S. PATENT DOCUMENTS

| | | | |
|---|---|---|---|
| 6,432,697 B1 * | 8/2002 | Tice et al. | 435/288.1 |
| 2011/0065157 A1 * | 3/2011 | Gorny et al. | 435/160 |
| 2013/0224853 A1 * | 8/2013 | van Walsem et al. | 435/292.1 |
| 2013/0302894 A1 * | 11/2013 | Bekele et al. | 435/394 |
| 2014/0186909 A1 * | 7/2014 | Calzia et al. | 435/134 |

* cited by examiner

*Primary Examiner* — Nathan Bowers
(74) *Attorney, Agent, or Firm* — Schwegman Lundberg & Woessner, P.A.

(57) ABSTRACT

The present invention relates to multilayered structures. In various embodiments, the present invention provides an at least partially transparent multilayered structure that includes at least one first layer including at least one polyolefin, and at least one second layer including at least one of a cyclic olefin copolymer and a cyclic olefin polymer. In various embodiments, the present invention provides methods of making such multilayered structures, and photobioreactors having compartments including such multilayered structures.

18 Claims, 1 Drawing Sheet

US 9,359,588 B2

MULTILAYERED STRUCTURE INCLUDING CYCLIC OLEFIN POLYMER OR COPOLYMER, AND PHOTOBIOREACTOR INCLUDING THE SAME

BACKGROUND OF THE INVENTION

A photobioreactor (PBR) is a bioreactor that includes one or more phototrophic organisms suspended in volume of liquid enclosed in a compartment that is at least partially transparent and that is exposed to light. PBRs can be used to cultivate or farm phototrophic organisms in high concentrations while preventing contamination from other undesired organisms, and can allow for a high degree of control over conditions such as pH, light intensity, carbon dioxide concentration, and temperature.

The materials forming the walls of the compartments in a PBR must allow for high light transmittance while also maintaining adequate strength over long time periods in wet environments.

SUMMARY OF THE INVENTION

In various embodiments, the present invention provides a photobioreactor. The photobioreactor includes at least one compartment. The compartment includes an interior and at least one wall. The interior is adapted to hold a liquid and a phototrophic biomaterial. The wall is at least partially transparent. The wall includes a multilayered structure. The wall includes at least one first layer including at least one polyolefin. The wall also includes at least one second layer including at least one of a cyclic olefin copolymer and a cyclic olefin polymer.

In various embodiments, the present invention provides a method of making a compartment wall for a photobioreactor. The method includes extruding a resin that includes at least one polyolefin. The method also includes extruding a resin that includes at least one of a cyclic olefin copolymer and a cyclic olefin polymer. The extruding of the resins forms a multilayered structure. The multilayered structure includes at least one first layer. The first layer includes at least one polyolefin. The multilayered structure also includes at least one second layer. The second layer includes at least one of a cyclic olefin copolymer and a cyclic olefin polymer.

In various embodiments, the present invention provides a photobioreactor. The photobioreactor includes at least one compartment. The compartment includes an interior and at least one wall, the interior adapted to hold a liquid and a phototrophic biological material. The wall is at least partially transparent and includes a multilayered structure. The multilayered structure includes layer a1), at least one first layer comprising at least one polyolefin. The multilayered structure also includes layer a2), at least one first layer including at least one polyolefin. The multilayered structure also includes layer a3), at least one first layer including at least one polyolefin. The multilayered structure also includes layer b1), at least one second layer including at least one of a cyclic olefin copolymer and a cyclic olefin polymer. The multilayered structure also includes layer b2), at least one second layer including at least one of a cyclic olefin copolymer and a cyclic olefin polymer. The multilayered structure also includes layer b3), at least one second layer including at least one of a cyclic olefin copolymer and a cyclic olefin polymer. The multilayered structure also includes layer c1) at least one first layer including at least one polyolefin. The multilayered structure also includes layer c2), at least one first layer including at least one polyolefin. The multilayered structure also includes layer c3), at least one first layer including at least one polyolefin. In the multilayered structure, layer a1) is in contact with layer a2), layer a2) is in contact with layer a3), layer a3) is in contact with layer b1), layer b1) is in contact with layer b2), layer b2) is in contact with layer b3), layer b3) is in contact with layer c1), layer c1) is in contact with layer c2), and layer c2) is in contact with layer c3).

In various embodiments, the present invention provides an at least partially transparent multilayered structure. The multilayered structure includes layer a), at least one first layer including at least one polyolefin. The multilayered structure also includes layer b), at least one second layer including at least one of a cyclic olefin copolymer and a cyclic olefin polymer. The multilayered structure also includes at least one first layer including at least one polyolefin. In the multilayered structure, layer a) is in contact with layer b), layer b) is in contact with layer c), and wherein at least one of layers a), b), and c) includes more than one first or second layer.

Various embodiments of the present invention provides certain advantages over other multilayered structures, PBRs including the same, and methods of making the same, at least some of which are unexpected. Some embodiments of the multilayered structure and a PBR wall including the multilayered structure have at least one of greater tensile strength, greater elongation %, higher modulus, longer lifetime, higher pressure at failure, higher light transmittance, less susceptibility to biofouling, including under wet or dry conditions, and lower cost, as compared to other multilayered structures. For example, a multilayered structure including polyolefin layers and one or more cylic olefin polymer or copolymer layers in place of one or more nylon layers can be less expensive; nylon requires an expensive tie layer to effectively fuse with polyolefin whereas various cyclic olefin polymers or copolymers require no tie layer to bond with polyolefin. In some embodiments, the multilayered structure can form a compartment for a photobioreactor that can be used to more efficiency cultivate a phototrophic organism than other photobioreactors, for example due to growing conditions that can lower production costs, higher growth rate due to higher light transmission, lower cost materials, operating conditions that lower harvesting costs, or less downtime for maintenance such as due to biofouling or leakage. In some examples, the multilayered structure can form a stronger compartment than other materials, lowering the rate of failure, and allowing material to be pumped through the bag at higher pressure or higher velocity than compartments made of other materials. The higher pressure or velocity can produce a greater amount of turbulence, causing more efficient growth of the biomaterial in the compartment due to even mixing of the biomaterial, for example allowing a more equal exposure to radiation. The higher pressure or velocity can shorten the amount of time required to harvest a biomaterial from the compartment. In some examples, the stronger material can be made into larger compartments.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
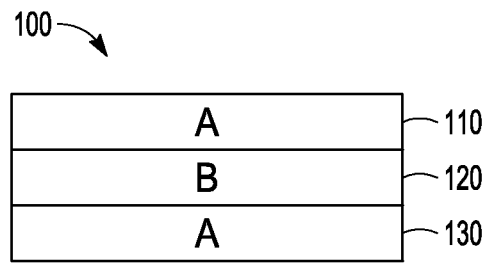
FIG. 1 illustrates a multilayered structure, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

DEFINITIONS

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values, and the endpoints of any sequence or range, is also disclosed.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "heterocyclyl" as used herein refers to aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

The terms "halo" or "halogen" or "halide", as used herein, by themselves or as part of another substituent mean, unless otherwise stated, a fluorine, chlorine, bromine, or iodine atom, preferably, fluorine, chlorine, or bromine.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number average molecular weight ($M_n$) is determined by analyzing a sample divided into molecular weight fractions of species i having $n_i$, molecules of molecular weight $M_i$ through the formula $M_n = \Sigma M_i n_i / \Sigma n_i$. The number average molecular weight can be measured by a variety of well-known methods including gel permeation chromatography, spectroscopic end group analysis and osmometry.

The term "light" as used herein refers to electromagnetic radiation in and near wavelengths visible by the human eye, and includes ultra-violet (UV) light and infrared light, from about 10 nm to about 300,000 nm wavelength.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "mil" as used herein refers to a thousandth of an inch, such that 1 mil=0.001 inch.

The term "polymer" as used herein can include a copolymer, unless otherwise indicated. In some embodiments, a polymer can include a copolymer. In other embodiments a polymer does not include a copolymer.

As used herein, the term "polyolefin" can include a polymer or copolymer.

As used herein, the term "10% secant modulus" refers to the ratio of stress to strain at the 10% strain point on the curve in a stress-strain diagram. It is the slope of a line from the origin to the 10% stain point on the stress-strain curve for the material.

Multilayered Structure.

In various embodiments, the present invention provides a multilayered structure. The structure can have the form of a plastic sheet or film. In some examples, the multilayered structure can be formed using coextrusion of any suitable combination of resins, followed by any suitable treatment such as coating, heat treatment, radiation treatment, or any combination thereof. Each layer is a flexible and planar arrangement of one or more materials. The multiple layers are fused together such that they together form a strong, flexible, at least partially transparent material. Any layer of the multilayered structure can include any suitable material, for example any suitable polymer or adhesive. Each layer can be partially or fully in contact with the one or more adjacent layers. For one layer to contact the other layer, the surface of one layer can be fused to the other, such that the planar distributions of material in each layer are adjacent to the another. In some examples, contacting can include at least some mixing of the materials in one layer with the other layer. In some examples, contacting can include a different material at the interface between layers due to a chemical reaction at the time of fusing or later, due to the application of adhesive between the layers, or a combination thereof. Two contacting layer having substantially all of the major side of at least one layer contacting at least part of the major side of another layer can be fully contacting one another. In another example, two layers can be fully contacting one another when substantially all of one major side of one layer is contacting substantially all of one major side of the other layer. Two layers can be partially contacting one another when a major side from one layer contacts the a major side of another layer, but less than all of a major side of one layer is contacting less than all of a major side of the other layer.

The multilayered structure is at least partially transparent; for example, either translucent or transparent. The multilayered structure can be substantially or fully transparent, or the multilayered structure can be only slightly transparent. The multilayered structure can have about 50% of the light transmittance of a fully transparent material, or about 60%, 70%, 80%, 90%, 95%, 96%, 96%, 97%, 98%, 99%, 99.5%, 99.9%, 99.99%, 99.999%, 99.9999%, or 99.99999% of the light transmittance of a fully transparent material. The multilayered structure can have substantially the same light transmissibility throughout, or it can have some locations that allow through different amounts of light than others.

The multilayered structure, and any layer within the multilayered structure, can have any suitable thickness. For example, any layer of the structure can have a thickness of about 0.01-30 mils, or about 0.1-20 mils, or about 1-10 mils. In some embodiments, the total thickness of all of the first layers and all of the second layers is about 0.1-50 mils, 1-30 mils, or about 2-20 mils. In some examples, the total thickness of the multilayered structure is substantially the same as the total thickness of all of the first layers and all of the second layers.

The multilayered structure can be used to form any suitable product. The multilayered structure can be formed into one or more bags or other shapes. For example, the structure can be cut to a desired size, or the structure can be sealed at a suitable location to fuse one section of the structure to another. For example, the multilayered structure can be used for any suitable purpose. For example, the multilayered structure can be used for packaging such as food packaging, plastic bags, labels, building construction, landscaping, electrical fabrication, photographic film, packaging such as food packaging or packaging for other commodities. In one example, the multilayered structure can be used to form one or more compartments of a photobioreactor.

Referring to FIG. 1, the multilayered structure 100 includes at least one first layer 110 and 130 (e.g., A layer) and at least one second layer 120 (e.g., B layer). The first layer 110 and 130 can include at least one polyolefin. The second layer 120 can include at least one of a cyclic olefin copolymer and a cyclic olefin polymer. In some examples, the at least one second layer 120 fully or partially contacts the at least one first layer 110 and 130. The multilayered structure can include at least two of the first layers 110 and 130, wherein the at least one second layer 120 can be between the at least two first layers 110 and 130. In some embodiments, the multilayered structure can include at least two or three second layers 120 (not shown in FIG. 1). At least two of the at least two or three second layers 120 can be in contact with one another.

Figure 2:
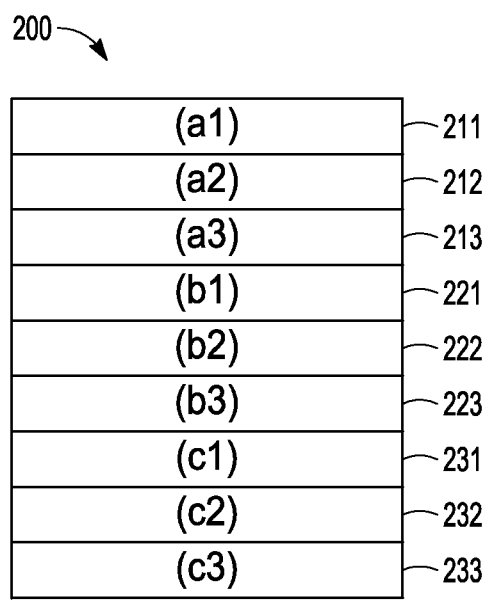
FIG. 2 illustrates a multilayered structure, in accordance with various embodiments.

The multilayered structure can include any number of each of the first and second layers, as well as any other suitable layers, in any suitable arrangement with one another. In some embodiments, the multilayered structure can include at least two of the first layers, and at least two or three of the second layers. At least two of the at least two or three second layers can be in contact with one another. At least two or three second layers can be between the at least two first layers. In some embodiments, the multilayered structure can include layer a), at least one first layer; layer b), at least one second layer; and layer c) at least one first layer. Layer a) can be in contact with layer b), and layer b) can be in contact with layer c). In some examples, the multilayered structure can include layer a1), at least one first layer; layer a2), at least one first layer; layer b1), at least one second layer; layer b2), at least one second layer; layer c1), at least one first layer; and layer c2), at least one first layer. Layer a1) can be in contact with layer a2), layer a2) can be in contact with layer b1), layer b1) can be in contact with layer b2), layer b2) can be in contact with layer c1), and layer c1) can be in contact with layer c2). Referring to FIG. 2 in another example, the multilayered structure 200 can have layer a1), at least one first layer 211; layer a2), at least one first layer 212; layer a3), at least one first layer 213; layer b1) at least one second layer 221; layer b2), at least one second layer 222; layer b3), at least one second layer 223; layer c1) at least one first layer 231; layer c2), at least one first layer 232; and layer c3), at least one first layer 233. Layer a1) 211 can be in contact with layer a2) 212, layer a2) 212 can be in contact with layer a3) 213, layer a3) 213 can be in contact with layer b1) 221, layer b1) 221 can be in contact with layer b2) 222, layer b2) 222 can be in contact with layer b3) 223, layer b3) 223 can be in contact with layer c1) 231, layer c1) 231 can be in contact with layer c2) 232, and layer c2) 232 can be in contact with layer c3) 233.

At Least One First Layer.

The multilayered structure includes at least one first layer. The multilayered structure can include any suitable number of first layers, such as 1, 2, 3, 4, 5, 6, 7, 8, 9, or 10 first layers, having any suitable arrangement with the other layers. The first layer includes at least one polyolefin, and can include any other suitable components. The polyolefin can be any suitable polyolefin. For example, the polyolefin can be a polymer formed from ($C_2$-$C_{10}$)alkene, such that it is a poly($C_2$-$C_{10}$)alkene. In another embodiment, the polymer is a copolymer, such as a random copolymer, and is formed from more than one ($C_2$-$C_{10}$)alkene, such as ethylene and a ($C_2$-$C_{10}$)alkene. In some embodiments, the polyolefin is a propylene polymer. In some embodiments, the polyolefin is at least one of a polyethylene or an ethylene copolymer. Polyethylene is a polymer formed by polymerizing ethylene, $H_2C{=}CH_2$. An ethylene copolymer is a copolymer formed by copolymerizing ethylene with another monomer. In various embodiments, the at least one first layer does not include cyclic olefin polymer or cyclic olefin copolymer; in other embodiments, the at least one first layer includes cyclic olefin polymer or cyclic olefin copolymer.

In some examples, the at least one first layer includes at least one of ultra high molecular weight polyethylene (UHMWPE), high-density polyethylene (HDPE), cross-linked polyethylene (PEX or XLPE), medium density polyethylene (MDPE), linear low-density polyethylene (LLDPE), low-density polyethylene (LDPE), very low-density polyethylene (VLDPE), and a copolymer thereof.

In various embodiments, the polyolefin in the at least one first layer can include a polymer formed from at least one of propene, butene, pentene, heptene, hexene, octene, nonene, and decene, or a copolymer formed from one or more of these alkenes and ethylene. In various embodiments, the polyolefin can include a polymer formed from at least one of ethylene, ($C_1$-$C_{10}$)alkylenoic acids (e.g. methylacrylic acid), vinyl ($C_1$-$C_{10}$)alkanoate esters (e.g., vinyl acetate), ($C_1$-$C_{10}$)alkyl ($C_1$-$C_{10}$)alkylenoate esters (e.g., methyl methacrylate, ethyl acrylate), and a copolymer formed from one or more these alkenes and ethylene (e.g., ethylene-vinyl acetate, ethylene-methacrylic acid, ethylene-ethyl acrylate, ethylene-n-butyl acrylate). In various embodiments, a copolymer formed from one or more ($C_1$-$C_{10}$)alkenes and ethylene can have about 0.0001 mol % repeating units derived from ethylene, or about 0.001, 0.01, 0.1, 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, or about 99.9999% repeating units derived from ethylene. A copolymer formed from one or more ($C_1$-$C_{10}$)alkenes and ethylene can have about 0.0001 mol % repeating units derived from the one or more ($C_1$-$C_{10}$)alkenes, or about 0.001, 0.01, 0.1, 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, or about 99.9999% repeating units derived from the one or more ($C_1$-$C_{10}$)alkenes. Herein, alkenes can be branched or linear, and can have a double bond at any suitable position therein. For example, decene can include dec-1-ene, dec-2-ene, dec-3-ene, dec-4-ene, dec-5-ene, dec-6-ene, dec-7-ene, dec-8-ene, dec-9-ene, any combination thereof, or any branched isomer thereof.

The first layers can independently and together form any suitable wt % of the total mass of the multilayered structure, or of all the first layers and of all the second layers, immediately after extrusion or after any suitable amount of further processing (e.g. drying, curing, heating, and the like), or any combination thereof. For example, all of the first layers can be, together, about 25-99 wt %, 50-95 wt %, or about 70-90 wt % of the total mass of all of the first layers and all of the second layers. For example, each of the first layers can be about 1-99 wt %, 2-60 wt %, or about 5-30 wt % of the total mass of all of the first layers and all of the second layers. In some embodiments, the total mass of the multilayered structure, immediately after extrusion or after any suitable amount of further processing, can be the same or different than the total mass of all the first layer and all the second layers.

The first layers can independently and together form any suitable % of the total thickness of the multilayered structure, or of the total thickness of all of the first layers and all of the second layers, immediately after extrusion of after any suitable amount of further processing (e.g. drying, curing, heating, and the like), or any combination thereof. For example, all of the first layers together can be about 25-99%, 50-95%, or about 70-90% of the total thickness of all of the first layers and all of the second layers. For example, each of the first layers can be about 1-99%, 2-60%, or about 5-30% of the total thickness all of the first layers and all of the second layers. In some embodiments, the total thickness of the multilayered structure, immediately after extrusion or after any suitable amount of further processing, can be the same or different than the total thickness of all the first layer and all the second layers.

At Least One Second Layer.

The multilayered structure includes at least one second layer. The multilayered structure can include any suitable number of second layers, such as 1, 2, 3, 4, 5, 6, 7, 8, 9, or 10 second layers, having any suitable arrangement with the other layers. The second layer includes at least one of a cyclic olefin copolymer and a cyclic olefin polymer, and can include any other suitable components. A cyclic olefin polymer is a polymer formed by polymerizing a cyclic olefin. A cyclic olefin copolymer is a copolymer formed by copolymerizing a cyclic olefin with another polymerizable material, such as ethylene.

In some examples, the at least one second layer includes a polymer or copolymer of at least one cyclic olefin selected from 8,9,10-trinorborn-2-ene ("norbornene"), 8,9,10-trinorborn-2-ene substituted at least one of the 5- and 6-position independently with $R^3$, 1,2,3,4,4a,5,8,8a-octahydro-1,4:5,8-dimethanonaphthalene ("tetracyclododecene"), and 1,2,3,4,4a,5,8,8a-octahydro-1,4:5,8-dimethanonaphthalene substituted at at least one of the 2- or 3-position with $R^3$. The variable $R^3$ at each occurrence can be independently selected from methyl, ethyl, propyl, butyl, and pentyl. The variable $R^3$ can be branched or unbranched.

In some embodiments, the at least one second layer includes a polymer or copolymer of at least one cyclic olefin having the structure (I)

(I)

Each carbon atom of structure (I) can be independently unsubstituted or substituted with $R^3$. The variables $R^1$ and $R^2$ at each occurrence can each be selected from J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, and $(C_1-C_{10})$heteroaryl$(C_0-C_{10})$alkyl, or $R^1$ and $R^2$ can together form structure (II)

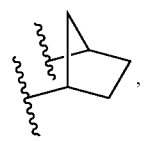

(II)

wherein each carbon atom of structure (II) can be independently unsubstituted or substituted with $R^3$. The variable $R^3$ at each occurrence can each be selected from J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, and $(C_1-C_{10})$heteroaryl$(C_0-C_{10})$alkyl. The variable J independently at each occurrence can be selected from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, OC(O)N$(R)_2$, $C(S)N(R)_2$, $(CH_2)_{0-2}NHC(O)R$, N(R)N(R)C(O)R, N(R)N(R)C(O)OR, N(R)N(R)C(O)N$(R)_2$, $N(R)SO_2R$, $N(R)SO_2N(R)_2$, N(R)C(O)OR, N(R)C(O)R, N(R)C(S)R, N(R)C(O)N$(R)_2$, N(R)C(S)N$(R)_2$, N(C(O)R)C(O)R, N(OR)R, C(=NH)N$(R)_2$, C(O)N(OR)R, and C(=NOR)R. The variable R at each occurrence can independently be selected from the group consisting of hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl. In $R^1$, $R^2$, $R^3$, and J, each alkyl, cycloalkyl, cycloalkylalkyl, aryl, aralkyl, heterocyclyl, heterocyclylalkyl, heteroaryl, heteroarylalkyl, can be independently unsubstituted or substituted with 1-3 J.

The cyclic olefin polymer or copolymer can be formed using any suitable method; for example, at least one of chain polymerization and ring opening metathesis polymerization. The photobioreactor of claim 1, wherein at least one second layer includes a copolymer of a cyclic olefin and at least one of ethylene, propene, butene, pentene, heptene, hexene, octene, nonene, and decene. In various embodiments, the copolymer of the cyclic olefin in the second layer can include a copolymer formed from one or more of ethylene, $(C_1-C_{10})$ alkylenoic acids (e.g. methylacrylic acid), vinyl $(C_1-C_{10})$alkanoate esters (e.g., vinyl acetate), and $(C_1-C_{10})$alkyl $(C_1-C_{10})$alkylenoate esters (e.g., methyl methacrylate, ethyl acrylate). The at least one second layer can include a copolymer of ethylene and at least one cyclic olefin selected from 8,9,10-trinorborn-2-ene (norbornene), 1,2,3,4,4a,5,8,8a-octahydro-1,4:5,8-dimethanonaphthalene (tetracyclododecene). In various embodiments, a copolymer formed from one or more $(C_1-C_{10})$alkenes and one or more cyclic olefins can have about 0.0001 mol % repeating units derived from ethylene, or about 0.001, 0.01, 0.1, 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, or about 99.9999% repeating units derived from ethylene. A copolymer formed from one or more $(C_1-C_{10})$alkenes and one or more cyclic olefins can have about 0.0001 mol % repeating units derived from the one or more $(C_1-C_{10})$alkenes, or about 0.001, 0.01, 0.1, 1, 2, 3, 4, 5, 10, 15, 20, 25, 30, 35, 40, 45, 50, 55, 60, 65, 70, 75, 80, 85, 90, 95, 96, 97, 98, 99, 99.9, 99.99, 99.999, or about 99.9999% repeating units derived from the one or more $(C_1-C_{10})$alkenes.

The second layers can independently and together form any suitable wt % of the total mass of the multilayered structure, or of all the first layers and of all the second layers, immediately after extrusion or after any suitable amount of further processing (e.g. drying, curing, heating, and the like), or any combination thereof. For example, all of the second layers can together be about 1-75 wt %, 5-50 wt %, or about 10-35 wt % of the total mass of all of the first layer and all of the second layers. Each of the second layers can be about 1-75 wt %, 2-50 wt %, 3-20 wt %, or about 5-15 wt % of the total mass of all of the first layers and all of the second layers.

The second layers can independently and together form any suitable % of the total thickness of the multilayered structure, or of the total thickness of all of the first layers and all of the second layers, immediately after extrusion of after any suitable amount of further processing (e.g. drying, curing, heating, and the like), or any combination thereof. For example, all of the second layers together can be about 1-75%, 5-50%, or about 10-35% of the total thickness of all of the first layers and all of the second layers. Each of the second layers can be about 1-75%, 2-50%, 3-20%, or about 5-15% of the total thickness all of the first layers and all of the second layers.

In some embodiments, the resin that forms the second layer can include polyolefin resin, such as any polyolefin described herein as being included in the first layer. In various embodiments, the resin that forms the second layer can include about 0.0001 wt % polyolefin resin, or about 0.001, 0.01, 0.1, 1, 2, 3, 4, 5, 10, 15, 20, 25, 30, 35, 40, 45, 50 wt % polyolefin resin.
Optional Ingredients.

In some examples, any layer in the multilayered structure can include any suitable optional ingredient. In some examples, one or more optional ingredients are present in one or more layers; in other embodiments, one or more optional ingredients are not present in the multilayered structure. Optional ingredients can be added during any suitable stage of making the multilayered structure; for example, the optional ingredient can be added to the resin, or can be added to the structure after extrusion.

In various embodiments, at least one of the first layers, at least one of the second layers, or a combination thereof, independently further includes at least one of a surfactant, emulsifier, dispersant, polymeric stabilizer, crosslinking agent, combination of polymers, catalyst, rheology modifier, density modifier, aziridine stabilizer, cure modifiers, free radical initiator, polymer, diluent, acid acceptor, antioxidant, heat stabilizer, flame retardant, scavenging agent, foam stabilizer, solvent, plasticizer, filler, inorganic particles, pigment, dye, dessicant, adhesion promoter, heat stabilizer, UV stabilizer, UV absorber, polyolefin, and flow control additive.
Photobioreactor.

Various embodiments of the present invention provide a photobioreactor. The photobioreactor can have any suitable design. The photobioreactor can include at least one compartment. The photobioreactor can include a plurality of compartments. The compartment can be any suitable shape and size. The compartment includes an interior that is defined by at least one wall. The interior of the compartment can hold a liquid and a phototrophic biomaterial. The liquid can be, for example, water, a solution of suitable compounds in water, or any liquid that can be used to cultivate the phototrophic biomaterial. The wall can be formed from any of the multilayer structures described herein.

The biomaterial can be least one phototrophic organism, such as algae, microalgae, and cyanobacteria.
Physical Properties of Multilayered Structure.

The multilayered structure can have any suitable physical properties. In some examples, the multilayered has physical properties that make it particularly suitable for particular uses, such as photobioreactor compartment walls.

As used herein, wet conditions can include partial or total immersion of the multilayered substrate in water, the multilayered structure being filled to any level with water, contacting with water vapor, or a combination thereof. Dry conditions can include no or minimal water contacting the multilayered substrate.

The multilayered structure can have any suitable average pressure at failure, in wet or dry conditions, at any suitable temperature; herein, the average pressure at failure is expressed as the air pressure within a compartment with walls formed from the multilayered structure. In some examples, the average pressure at failure of the multilayered structure can be about 10-100 psi, 11-50 psi, or about 13-30 psi. The average pressure at failure of the multilayered structure under dry conditions, expressed as the air pressure within the compartment, can be about 20-40 psi. The average pressure at failure of the multilayered structure under wet conditions can be about 10-20 psi. The average pressure at failure of the multilayered structure under wet conditions of the multilayered structure at about 130° F. can be about 10-20 psi.

The multilayered structure can have any suitable average stress at failure (e.g. wall stress or hoop stress), in wet or dry conditions, at any suitable temperature. In some examples the average stress at failure can be about 250 psi-3000 psi, or about 500-2500 psi, or about 700-1900 psi, or about 1500-2000 psi.

The multilayered structure can have any suitable average % elongation, in wet or dry conditions, at any suitable temperature. For example, the average % elongation of the multilayered structure at about 23° C. under dry conditions can be about 300-2500%, 400-1500%, 350-1000%, or about 550-650%. The average % elongation of the multilayered structure at about 23° C. under wet conditions can be about 300-2500%, 400-1500%, 350-1000%, or about 550-650%. The average % elongation of the multilayered structure at about 66° C. under dry conditions can be about 300-2500%, 500-2000%, 700-1500%, or about 1150-1300%. The average % elongation of the multilayered structure at about 66° C. under wet conditions can be about 300-2500%, 400-2700%, 600-1500%, or about 900-1050%.

The multilayered structure can have any suitable average max load, in wet or dry conditions, at any suitable temperature. For example, the average max load of the multilayered structure at about 23° C. under dry conditions can be about 5-70 lbf, 10-50 lbf, or about 20-30 lbf. The average max load of the multilayered structure at about 23° C. under wet conditions can be about 5-70 lbf, 10-50 lbf, or about 20-30 lbf. The average max load of the multilayered structure at about 66° C. under dry conditions can be about 5-70 lbf, 10-60 lbf, or about 17-27 lbf. The average max load of the multilayered structure at about 66° C. under wet conditions can be about 5-70 lbf, 10-50 lbf, or about 17-27 lbf.

The multilayered structure can have any suitable average modulus, in wet or dry conditions, at any suitable temperature. For example, the average 10% secant modulus of the multilayered structure at about 23° C. under dry conditions can be about 5,000-150,000 psi, 50,000-120,000 psi or about 73,000-93,000 psi. The average 10% secant modulus of the multilayered structure at about 23° C. under wet conditions can be about 5,000-150,000 psi, 70,000-130,000 psi, or about 92,000-112,000 psi. The average 10% second modulus of the multilayered structure at about 66° C. under dry conditions can be about 5,000-150,000 psi, 15,000-100,000 psi, or about 32,000-52,000 psi. The average 10% secant modulus of the multilayered structure at about 66° C. under wet conditions can be about 5,000-150,000 psi, 20,000-100,000 psi, or about 40,000-60,000 psi.

Method of Making a Multilayered Structure.

In various embodiments, the present invention provides a method of making any of the multilayered structures described herein. For example, the method can include extruding (e.g. coextruding) one or more resins. In some examples, the method can include extruding a plurality of resins, wherein each layer is extruded from at least one of the resins. The resin can include any suitable material, including any optional ingredients described herein. The method can include extruding a resin including at least one polyolefin. The method can also include extruding a resin including at least one of a cyclic olefin copolymer and a cyclic olefin polymer. The extruded resins form any multilayered structure described herein. For example, the extruded resins form a multilayered structure including at least one first layer including at least one polyolefin, and including at least one second layer including at least one of a cyclic olefin copolymer and a cyclic olefin polymer.

The extrusion can be conducted with any suitable equipment. The extrusion can be, for example, at least one of cast sheet extrusion, cast film extrusion, blown sheet extrusion, and blown film extrusion.

EXAMPLES

The present invention can be better understood by reference to the following examples which are offered by way of illustration. The present invention is not limited to the examples given herein.

The 62 metallocene was MarFlex® D163, linear low density polyethylene, a copolymer of hexene and ethylene produced using a metallocene catalyst, provided by Chevron Phillips Chemical Company LLC. The 82 octene was DOWLEX™ 2045 G polyethylene resin, linear low density polyethylene, a copolymer of octene and ethylene produced using a Ziegler-Natta catalyst, provided by the Dow Chemical Company. The 28 tie was DuPont™ Bynel® 4157, an anhydride-modified, linear low-density polyethylene resin provided by DuPont™. The Nylon was UBE Nylon 5033B, provided by UBE Engineering Plastics S.A.

The Topas 8007-F400 was a copolymer of ethylene and norbornene, provided by TOPAS®, having: a volume flow index MVR at 260° C., 2.16 kg, using ISO 1133, of 32 ml/10 min; a volume flow index MVR at HDT+115° C., 2.16 kg, using ISO 1133, of 2 ml/10 min; a density, using ISO 1183, of 1.02 g/cm$^3$; a water absorption (24 h immersion in water at 23° C.), using ISO 62, of <0.01%; water vapor permeability (at 23 C and 85% relative humidity), using DIN 53 122, of 0.023 g·mm/m$^2$·d; a mold shrinkage (60° C., 2 mm wall thickness) of 0.4-0.7; tensile strength [5 mm/min], using ISO 527 parts 1 and 2, of 63 MPa; elongation at break [5 mm/min], using ISO 527 parts 1 and 2, of 10% (with a yield strain of 4.5%); tensile modulus [1 mm/min], using ISO 527 parts 1 and 2, of 2600 MPa; a Charpy impact strength, using ISO 179/1eU, of 20 kJ/m$^2$; a notched Charpy impact strength, using ISO 179/1eA, of 2.6 kJ/m$^2$; and a ball indentation hardness, 30-second value, using ISO 2039 part 1, with an applied load of 961 N, of 130 N/mm$^2$; a heat deflection temperature HDT/B (0.45 MPa), using ISO 75 parts 1 and 2, of 75° C.; a coefficient of linear thermal expansion, using ISO 11 359 parts 1 and 2, of 0.7×10$^{-4}$K$^{-1}$; and a light transmission (2 mm wall thickness), using ISO 13468-2, of 91%.

The Topas 6013F-04 was a copolymer of ethylene and norbornene, provided by TOPAS®, having: a volume flow index MVR at 260° C., 2.16 kg, using ISO 1133, of 14 ml/10 min; a volume flow index MVR at HDT+115° C., 2.16 kg, using ISO 1133, of 6 ml/10 min; a density, using ISO 1183, of 1.02 g/cm$^3$; a water absorption (24 h immersion in water at 23° C.), using ISO 62, of <0.01%; water vapor permeability (at 23 C and 85% relative humidity), using DIN 53 122, of 0.035 g·mm/m$^2$·d; a mold shrinkage (60° C., 2 mm wall thickness) of 0.4-0.7; tensile strength [5 mm/min], using ISO 527 parts 1 and 2, of 63 MPa; elongation at break [5 mm/min], using ISO 527 parts 1 and 2, of 2.7%; tensile modulus [1 mm/min], using ISO 527 parts 1 and 2, of 2900 MPa; a Charpy impact strength, using ISO 179/1eU, of 15 kJ/m$^2$; a notched Charpy impact strength, using ISO 179/1eA, of 1.8 kJ/m$^2$; and a ball indentation hardness, 30-second value, using ISO 2039 part 1, with an applied load of 961 N, of 184 N/mm$^2$; a heat deflection temperature HDT/B (0.45 MPa), using ISO 75 parts 1 and 2, of 130° C.; a coefficient of linear thermal expansion, using ISO 11 359 parts 1 and 2, of 0.6×10$^{-4}$ K$^{-1}$ and a light transmission (2 mm wall thickness), using ISO 13468-2, of 91%.

Example 1 (Comparative)

A 9-layer extruded plastic sheet (9 mils thick, 20 inches wide, and 500 ft long) was formed using a 9 layer blown film line, manufactured by Brampton. The sheet had the layers indicated in Table 1. Three test bags were fabricated from the extruded plastic, were thermally sealed, and had dimensions of about 20 inches wide and 90 inches long.

The bags were then subjected to a pressure failure test, designed to mimic creep failure conditions, using an Integra bag tester, by inflating the bags to 12 psi overnight (about 8 hours) and then increasing the pressure at a rate 0.001 psi/s. The bags tested at an average wall stress or hoop stress of 1437 psi at failure, with all failures occurring in the parent material (not seal failures). The test required about 12 hours, including about 4 hours of the pressure ramp up.

TABLE 1

| | Nylon core. | | |
|---|---|---|---|
| Layer | Resin | Wt % of Layer | Wt % of Batch |
| 1 (outside) | 62 metallocene | 100% | 7% |
| 2 | 62 metallocene | 100% | 27% |
| 3 | 28 tie | 100% | 6% |
| 4 | Nylon | 100% | 7% |
| 5 | Nylon | 100% | 6% |

TABLE 1-continued

Nylon core.

| Layer | Resin | Wt % of Layer | Wt % of Batch |
|---|---|---|---|
| 6 | Nylon | 100% | 7% |
| 7 | 28 tie | 100% | 6% |
| 8 | 62 metallocene | 100% | 27% |
| 9 (outside) | 62 metallocene | 100% | 7% |

Example 2

COC Core Pressure Test

A 9-layer extruded plastic sheet having the same dimensions as the sheet constructed in Comparative Example 1 was formed using the procedure described in Example 1 and having the layers indicated in Table 2. Three test bags were fabricated from the extruded plastic layer, having the same dimensions and fabrication method as that described in Example 1. The three bags were tested in the same fashion as described in Example 1. The average was stress or hoop stress at failure was 1738 psi, with all failures occurring in the parent material (not seal failures), a 21% improvement over Example 1.

TABLE 2

COC core.

| Layer | Resin | Wt % of Layer | Wt % of Batch |
|---|---|---|---|
| 1 (outside) | 62 metallocene | 100% | 7% |
| 2 | 62 metallocene | 100% | 27% |
| 3 | 82 octene | 100% | 6% |
| 4 | Topas 8007-F400 | 100% | 7% |
| 5 | Topas 8007-F400 | 100% | 6% |
| 6 | Topas 8007-F400 | 100% | 7% |
| 7 | 82 octene | 100% | 6% |

TABLE 2-continued

COC core.

| Layer | Resin | Wt % of Layer | Wt % of Batch |
|---|---|---|---|
| 8 | 62 metallocene | 100% | 27% |
| 9 (outside) | 62 metallocene | 100% | 7% |

Example 3 (Comparative)

Nylon Core, Pressure Test with Water and Heating

Three nylon-containing bags were fabricated as described in Example 1.

About 2 cups of water was put into the bags, and the bags were floated in a heated water bath at about 130° F. The bags were held at 4 psi overnight (e.g. about 8 hours) and then the pressure was increased at a rate of 0.001 psi/s until failure. The average was stress or hoop stress at failure was 854 psi, with all failures occurring in the parent material (not seal failures).

Example 4

COC Core, Pressure Test with Water and Heating

Three COC-containing bags were fabricated as described in Example 2.

A similar testing procedure was conducted as described in Example 3. The average wall stress or hoop stress at failure was 901 psi, with all failures occurring in the parent material (not seal failures), a 6% increase over Example 3.

Example 5 (Comparative)

Nylon Core, Physical Testing

Tensile tests were performed using specimens (1"×8") of the plastic sheet formed in Example 1, using both dry samples and samples that had been soaked in water for about 2-3 days. Tensile tests were performed as per ASTM D882 at 23° C. and 66° C. for each sample.

Results are given in Table 3, wherein MD indicates "machine direction" and TD indicates "transverse direction.".

TABLE 3

Physical properties of the plastic sheet of Comparative Example 1.

| Property | Method | | Example 1 dry 23° C. | | Example 1 wet 23° C. | | Example 1 dry 66° C. | | Example 1 wet 66° C. |
|---|---|---|---|---|---|---|---|---|---|
| Elongation (%) stand. dev. | ASTM D 882 | MD | 1149.9 167.8 | MD | 1410.9 103.3 | MD | 1098.5 88.8 | MD | 1235.4 111.8 |
| | | TD | 1279.2 103.0 | TD | 1699.5 130.5 | TD | 1222.2 72.0 | TD | 1382.0 49.2 |
| | | AVG | 1214.5 98.4 | AVG | 1555.2 83.2 | AVG | 1160.3 57.2 | AVG | 1308.7 61.1 |
| Max load (lbf) stand. dev | ASTM D 882 | MD | 37.4 3.3 | MD | 43.3 3.4 | MD | 29.8 3.6 | MD | 32.2 3.5 |
| | | TD | 39.1 2.7 | TD | 45.2 3.2 | TD | 28.9 2.1 | TD | 32.0 2.6 |
| | | AVG | 38.3 2.1 | AVG | 44.3 2.3 | AVG | 29.3 2.1 | AVG | 32.1 2.2 |
| 10% Secant modulus (psi) stand. dev. | ASTM D 882 | MD | 40557.0 14206.0 | MD | 53169.0 5493.0 | MD | 19834.0 2868.0 | MD | 18248.0 5776.0 |
| | | TD | 40744.0 7316.0 | TD | 50590.0 4948.0 | TD | 20574.0 1258.0 | TD | 20310.0 2256.0 |
| | | AVG | 40651.0 7989.0 | AVG | 51879.0 3697.0 | AVG | 20204.0 1566.0 | AVG | 19279.0 3101.0 |

Example 6

COC Core, Physical Testing

Tensile tests were performed using specimens of the plastic sheet formed in Example 2, using both dry samples and samples that had been soaked in water for about 2-3 days. Tensile tests were performed at 23° C. and 66° C. for each sample, using the same procedure as described in Example 5. Results are given in Table 4, wherein MD indicates "machine direction" and TD indicates "transverse direction."

TABLE 4

Physical properties of plastic sheet of Example 2.

| Property | Method | | Example 2 dry 23° C. | | Example 2 wet 23° C. | | Example 2 dry 66° C. | | Example 2 wet 66° C. |
|---|---|---|---|---|---|---|---|---|---|
| Elongation (%) stand. dev. | ASTM D 882 | MD | 513.2 108.6 | MD | 630.7 108.8 | MD | 810.7 71.0 | MD | 699.9 64.6 |
| | | TD | 665.9 128.5 | TD | 591.2 147.6 | TD | 1666.7 396.3 | TD | 1263.5 414.1 |
| | | AVG | 589.5 84.1 | AVG | 610.9 91.7 | AVG | 1238.7 201.3 | AVG | 981.7 209.5 |
| Max load (lbf) stand. Dev | ASTM D 882 | MD | 25.4 2.6 | MD | 29.1 3.7 | MD | 20.0 1.1 | MD | 20.4 1.7 |
| | | TD | 24.9 2.8 | TD | 24.6 4.1 | TD | 23.3 3.2 | TD | 21.9 3.4 |
| | | AVG | 25.2 1.9 | AVG | 26.8 2.8 | AVG | 21.7 1.7 | AVG | 21.2 1.9 |
| 10% Secant Modulus (psi) stand. dev. | ASTM D 882 | MD | 83157.0 3992.0 | MD | 107268.0 7524.0 | MD | 45608.0 6938.0 | MD | 57244 4075 |
| | | TD | 83638.0 4602.0 | TD | 97832.0 10683.0 | TD | 37870.0 10880.0 | TD | 44098 8091 |
| | | AVG | 83398.0 3046.0 | AVG | 102550.0 6533.0 | AVG | 41739.0 6452.0 | AVG | 50671 4530 |

The wet specimens of Example 1 at both 23° C. and 66° C. showed 5-20% higher tensile properties compared to their dry counterparts, but the samples tested at 66° C. showed lower elongation and max load than those at 23° C. The tensile properties of the specimens of Example 2 were about 35-50% lower than the specimens of Example 1 at 23° C. and did not show a significant difference between the wet and dry samples. The max load of the specimens of Example 2 decreased by 15-20% at 66° C., but elongation increased by 40-50%, resulting in a similar elongation as the specimens of Example 1 at 66° C.

Example 7

COC Core Blend

A 9-layer extruded plastic sheet having similar dimensions to the sheet constructed in Example 1 was formed using the procedure described in Example 1 and having the layers indicated in Table 5. Three test bags were fabricated from the extruded plastic layer, having the same dimensions and fabrication method as that described in Example 1. The three bags were tested in the same fashion as described in Example 3. The average pressure at failure was 15.38 psi, with all failures occurring in the parent material (not seal failures), a 15.3% improvement over Example 3.

TABLE 5

COC core blend.

| Layer | Resin | Wt % of Layer | Wt % of Batch |
|---|---|---|---|
| 1 (outside) | 62 metallocene | 100% | 7% |
| 2 | 62 metallocene | 100% | 27% |
| 3 | 82 octene | 100% | 6% |
| 4 | Topas 8007-F400 | 50% | 7% |
| | Topas 6013F-04 | 50% | |

TABLE 5-continued

COC core blend.

| Layer | Resin | Wt % of Layer | Wt % of Batch |
|---|---|---|---|
| 5 | Topas 8007-F400 | 50% | 6% |
| | Topas 6013F-04 | 50% | |
| 6 | Topas 8007-F400 | 50% | 7% |
| | Topas 6013F-04 | 50% | |
| 7 | 82 octene | 100% | 6% |
| 8 | 62 metallocene | 100% | 27% |
| 9 (outside) | 62 metallocene | 100% | 7% |

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

Additional Embodiments

The present invention provides for the following exemplary embodiments, the numbering of which is not to be construed as designating levels of importance:

Embodiment 1 provides a photobioreactor, comprising: at least one compartment comprising an interior and at least one wall, the interior adapted to hold a liquid and a phototrophic biomaterial, the wall being at least partially transparent and comprising a multilayered structure comprising at least one first layer comprising at least one polyolefin; and at least one second layer comprising at least one of a cyclic olefin copolymer and a cyclic olefin polymer.

Embodiment 2 provides the photobioreactor of Embodiment 1, wherein the at least one second layer contacts the at least one first layer.

Embodiment 3 provides the photobioreactor of any one of Embodiments 1-2, comprising at least two of the first layers, wherein the at least one second layer is between the at least two first layers.

Embodiment 4 provides the photobioreactor of any one of Embodiments 1-3, comprising at least two or three second layers.

Embodiment 5 provides the photobioreactor of Embodiment 4, wherein at least two of the at least two or three second layers are in contact with one another.

Embodiment 6 provides the photobioreactor of any one of Embodiments 1-5, comprising: at least two of the first layers; and at least two or three of the second layers; wherein at least two of the at least two or three second layers are in contact with one another, and wherein the at least two or three second layers are between the at least two first layers.

Embodiment 7 provides the photobioreactor of any one of Embodiments 1-6, comprising: a) at least one first layer; b) at least one second layer; and c) at least one first layer; wherein layer a) is in contact with layer b), and layer b) is in contact with layer c).

Embodiment 8 provides the photobioreactor of any one of Embodiments 1-7, comprising: a1) at least one first layer; a2) at least one first layer; b1) at least one second layer; b2) at least one second layer; c1) at least one first layer; and c2) at least one first layer; wherein layer a1) is in contact with layer a2), layer a2) is in contact with layer b1), layer b1) is in contact with layer b2), layer b2) is in contact with layer c1), and layer c1) is in contact with layer c2).

Embodiment 9 provides the photobioreactor of any one of Embodiments 1-8, comprising: a1) at least one first layer; a2) at least one first layer; a3) at least one first layer; b1) at least one second layer; b2) at least one second layer; b3) at least one second layer; c1) at least one first layer; c2) at least one first layer; and c3) at least one first layer; wherein layer a1) is in contact with layer a2), layer a2) is in contact with layer a3), layer a3) is in contact with layer b1), layer b1) is in contact with layer b2), layer b2) is in contact with layer b3), layer b3) is in contact with layer c1), layer c1) is in contact with layer c2), and layer c2) is in contact with layer c3).

Embodiment 10 provides the photobioreactor of any one of Embodiments 1-9, wherein the at least one first layer does not include cyclic olefin polymer or cyclic olefin copolymer.

Embodiment 11 provides the photobioreactor of any one of Embodiments 1-10, wherein the total thickness of all of the first layers and all of the second layers is about 1-30 mils.

Embodiment 12 provides the photobioreactor of any one of Embodiments 1-11, wherein the total thickness of the multilayered structure is substantially the same as the total thickness of all of the first layers and all of the second layers.

Embodiment 13 provides the photobioreactor of any one of Embodiments 1-12, wherein the polyolefin in the first layer comprises at least one of polyethylene and an ethylene copolymer.

Embodiment 14 provides the photobioreactor of any one of Embodiments 1-13, wherein at least one first layer comprises at least one of ultra high molecular weight polyethylene (UHMWPE), high-density polyethylene (HDPE), cross-linked polyethylene (PEX or XLPE), medium density polyethylene (MDPE), linear low-density polyethylene (LLDPE), low-density polyethylene (LDPE), very low-density polyethylene (VLDPE), and a copolymer thereof.

Embodiment 15 provides the photobioreactor of any one of Embodiments 1-14, wherein at least one first layer comprises a polymer of at least one of propene, butene, pentene, heptene, hexene, octene, nonene, decene, ethylene, a ($C_1$-$C_{10}$) alkylenoic acid, a vinyl ($C_1$-$C_{10}$)alkanoate ester, and a ($C_1$-$C_{10}$)alkyl ($C_1$-$C_{10}$)alkylenoate ester.

Embodiment 16 provides the photobioreactor of any one of Embodiments 1-15, wherein at least one first layer comprises a copolymer of ethylene and at least one of propene, butene, pentene, heptene, hexene, octene, nonene, decene, a ($C_1$-$C_{10}$) alkylenoic acid, a vinyl ($C_1$-$C_{10}$)alkanoate ester, and a ($C_1$-$C_{10}$)alkyl ($C_1$-$C_{10}$)alkylenoate ester.

Embodiment 17 provides the photobioreactor of any one of Embodiments 1-16, wherein all of the first layers are together about 25-99 wt % of the total mass of all of the first layers and all of the second layers.

Embodiment 18 provides the photobioreactor of any one of Embodiments 1-17, wherein all of the first layers are together about 70-90 wt % of the total mass of all of the first layers and all of the second layers.

Embodiment 19 provides the photobioreactor of any one of Embodiments 1-18, wherein each of the first layers are about 1-99 wt % of the total mass of all of the first layers and all of the second layers.

Embodiment 20 provides the photobioreactor of any one of Embodiments 1-19, wherein each of the first layers are about 5-30 wt % of the combination of the total mass of all of the first layers and all of the second layers.

Embodiment 21 provides the photobioreactor of any one of Embodiments 1-20, wherein each of the first layers are about 1-99% of the total thickness all of the first layers and all of the second layers.

Embodiment 22 provides the photobioreactor of any one of Embodiments 1-21, wherein each of the first layers are about 5-30% of the total thickness all of the first layers and all of the second layers.

Embodiment 23 provides the photobioreactor of any one of Embodiments 1-22, wherein all of the first layers are together about 25-99% of the total thickness of all of the first layers and all of the second layers.

Embodiment 24 provides the photobioreactor of any one of Embodiments 1-23, wherein all of the first layers are together about 70-90% of the total thickness of all of the first layers and all of the second layers.

Embodiment 25 provides the photobioreactor of any one of Embodiments 1-24, wherein at least one second layer comprises a polymer or copolymer of at least one cyclic olefin selected from 8,9,10-trinorborn-2-ene ("norbornene"), 8,9,10-trinorborn-2-ene substituted at at least one of the 5- and 6-position independently with $R^3$, 1,2,3,4,4a,5,8,8a-octahydro-1,4:5,8-dimethanonaphthalene ("tetracyclododecene"), and 1,2,3,4,4a,5,8,8a-octahydro-1,4:5,8-dimethanonaphthalene substituted at at least one of the 2- or 3-position with $R^3$, wherein $R^3$ at each occurrence is independently selected from methyl, ethyl, propyl, butyl, and pentyl, wherein $R^3$ is branched or unbranched.

Embodiment 26 provides the photobioreactor of any one of Embodiments 1-25, wherein at least one second layer comprises: a polymer or copolymer of at least one cyclic olefin having the structure (I)

(I)

wherein each carbon atom of structure (I) is independently unsubstituted or substituted with $R^3$; wherein $R^1$ and $R^2$ at each occurrence are each selected from J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, and $(C_1-C_{10})$heteroaryl$(C_0-C_{10})$alkyl, or wherein $R^1$ and $R^2$ together form structure (II)

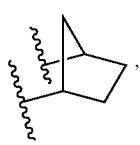

(II)

wherein each carbon atom of structure (II) is independently unsubstituted or substituted with $R^3$; wherein $R^3$ at each occurrence are each selected from J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, and $(C_1-C_{10})$heteroaryl$(C_0-C_{10})$alkyl; wherein J independently at each occurrence is selected from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-2}NHC(O)R$, N(R)N(R)C(O)R, N(R)N(R)C(O)OR, $N(R)N(R)C(O)N(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(C(O)R)C(O)R, N(OR)R, $C(=NH)N(R)_2$, C(O)N(OR)R, and C(=NOR)R, wherein R is independently at each occurrence selected from the group consisting of hydrogen, $(C_1-C_{10})$alkyl, $(C_1-C_{10})$cycloalkyl, $(C_1-C_{10})$cycloalkyl$(C_1-C_{10})$alkyl, $(C_1-C_{10})$aryl, $(C_1-C_{10})$aralkyl, $(C_1-C_{10})$heterocyclyl, $(C_1-C_{10})$heterocyclyl$(C_1-C_{10})$alkyl, $(C_1-C_{10})$heteroaryl, and $(C_1-C_{10})$heteroaryl$(C_1-C_{10})$alkyl; and wherein in $R^1$, $R^2$, $R^3$, and J, each alkyl, cycloalkyl, cycloalkylalkyl, aryl, aralkyl, heterocyclyl, heterocyclylalkyl, heteroaryl, heteroarylalkyl, is independently unsubstituted or substituted with 1-3 J.

Embodiment 27 provides the photobioreactor of Embodiment 26, wherein the cyclic olefin polymer or copolymer is formed by at least one of chain polymerization and ring opening metathesis polymerization.

Embodiment 28 provides the photobioreactor of any one of Embodiments 1-27, wherein at least one second layer comprises a copolymer of a cyclic olefin and at least one of ethylene, propene, butene, pentene, heptene, hexene, octene, nonene, decene, a $(C_1-C_{10})$alkylenoic acid, a vinyl $(C_1-C_{10})$ alkanoate ester, and a $(C_1-C_{10})$alkyl $(C_1-C_{10})$alkylenoate ester.

Embodiment 29 provides the photobioreactor of any one of Embodiments 1-28, wherein the at least one second layer comprises a copolymer of ethylene and at least one cyclic olefin selected from 8,9,10-trinorborn-2-ene (norbornene), 1,2,3,4,4a,5,8,8a-octahydro-1,4:5,8-dimethanonaphthalene (tetracyclododecene).

Embodiment 30 provides the photobioreactor of any one of Embodiments 1-29, wherein all of the second layers are together about 1-75 wt % of the total mass of all of the first layers and all of the second layers.

Embodiment 31 provides the photobioreactor of any one of Embodiments 1-30, wherein all of the second layers are together about 10-35 wt % of the total mass of all of the first layers and all of the second layers.

Embodiment 32 provides the photobioreactor of any one of Embodiments 1-31, wherein each of the second layers are about 1-75 wt % of the total mass of all of the first layers and all of the second layers.

Embodiment 33 provides the photobioreactor of any one of Embodiments 1-32, wherein each of the second layers are about 5-15 wt % of the total mass of all of the first layers and all of the second layers.

Embodiment 34 provides the photobioreactor of any one of Embodiments 1-33, wherein each of the second layers are about 1-75% of the total thickness all of the first layers and all of the second layers.

Embodiment 35 provides the photobioreactor of any one of Embodiments 1-34, wherein each of the second layers are about 5-15% of the total thickness all of the first layers and all of the second layers.

Embodiment 36 provides the photobioreactor of any one of Embodiments 1-35, wherein all of the second layers are together about 1-75% of the total thickness of all of the first layers and all of the second layers.

Embodiment 37 provides the photobioreactor of any one of Embodiments 1-36, wherein all of the second layers are together about 10-30% of the total thickness of all of the first layers and all of the second layers.

Embodiment 38 provides the photobioreactor of any one of Embodiments 1-37, wherein at least one of the first layers, at least one of the second layers, or a combination thereof, independently further comprises at least one of a surfactant, emulsifier, dispersant, polymeric stabilizer, crosslinking agent, combination of polymers, catalyst, rheology modifier, density modifier, aziridine stabilizer, cure modifiers, free radical initiator, polymer, diluent, acid acceptor, antioxidant, heat stabilizer, flame retardant, scavenging agent, foam stabilizer, solvent, plasticizer, filler, inorganic particles, pigment, dye, dessicant, adhesion promoter, heat stabilizer, UV stabilizer, UV absorber, polyolefin, and flow control additive.

Embodiment 39 provides the photobioreactor of any one of Embodiments 1-38, wherein the multilayered structure is extruded using at least one of cast sheet extrusion, cast film extrusion, blown sheet extrusion, and blown film extrusion.

Embodiment 40 provides the photobioreactor of any one of Embodiments 1-39, wherein the multilayered structure is extruded from a plurality of resins, wherein each layer is extruded from at least one of the resins.

Embodiment 41 provides the photobioreactor of Embodiment 40, wherein the resin from which at least one of the at least one first layer is extruded, the resin from which at least one of the at least one second layer is extruded, or a combination thereof, independently further comprises at least one of a surfactant, emulsifier, dispersant, polymeric stabilizer, crosslinking agent, combination of polymers, catalyst, rheology modifier, density modifier, aziridine stabilizer, cure modifiers, free radical initiator, polymer, diluent, acid acceptor, antioxidant, heat stabilizer, flame retardant, scavenging agent, foam stabilizer, solvent, plasticizer, filler, inorganic particles, pigment, dye, dessicant, adhesion promoter, heat stabilizer, UV stabilizer, UV absorber, polyolefin, and flow control additive.

Embodiment 42 provides the photobioreactor of any one of Embodiments 1-41, wherein the average pressure at failure of the multilayered structure is about 10-100 psi.

Embodiment 43 provides the photobioreactor of any one of Embodiments 1-42, wherein the average stress at failure of the multilayered structure is about 250-3000 psi.

Embodiment 44 provides the photobioreactor of any one of Embodiments 1-43, wherein the average pressure at failure of the multilayered structure under dry conditions is about 20-40 psi.

Embodiment 45 provides the photobioreactor of any one of Embodiments 1-44, wherein the average pressure at failure of the multilayered structure under wet conditions is about 10-20 psi.

Embodiment 46 provides the photobioreactor of any one of Embodiments 1-45, wherein the average pressure at failure of the multilayered structure under wet conditions of the multilayered structure at about 130° F. is about 10-20 psi.

Embodiment 47 provides the photobioreactor of any one of Embodiments 1-46, wherein the average % elongation of the multilayered structure at about 23° C. under dry conditions is about 300-2500%.

Embodiment 48 provides the photobioreactor of any one of Embodiments 1-47, wherein the average % elongation of the multilayered structure at about 23° C. under dry conditions is about 550-650%.

Embodiment 49 provides the photobioreactor of any one of Embodiments 1-48, wherein the average % elongation of the multilayered structure at about 23° C. under wet conditions is about 300-2500%.

Embodiment 50 provides the photobioreactor of any one of Embodiments 1-49, wherein the average % elongation of the multilayered structure at about 23° C. under wet conditions is about 550-650%.

Embodiment 51 provides the photobioreactor of any one of Embodiments 1-50, wherein the average % elongation of the multilayered structure at about 66° C. under dry conditions is about 300-2500%.

Embodiment 52 provides the photobioreactor of any one of Embodiments 1-51, wherein the average % elongation of the multilayered structure at about 66° C. under dry conditions is about 1150-1300%.

Embodiment 53 provides the photobioreactor of any one of Embodiments 1-52, wherein the average % elongation of the multilayered structure at about 66° C. under wet conditions is about 300-2500%.

Embodiment 54 provides the photobioreactor of any one of Embodiments 1-53, wherein the average % elongation of the multilayered structure at about 66° C. under wet conditions is about 900-1050%.

Embodiment 55 provides the photobioreactor of any one of Embodiments 1-54, wherein the average max load of the multilayered structure at about 23° C. under dry conditions is about 5-70 lbf.

Embodiment 56 provides the photobioreactor of any one of Embodiments 1-55, wherein the average max load of the multilayered structure at about 23° C. under dry conditions is about 20-30 lbf.

Embodiment 57 provides the photobioreactor of any one of Embodiments 1-56, wherein the average max load of the multilayered structure at about 23° C. under wet conditions is about 5-70 lbf.

Embodiment 58 provides the photobioreactor of any one of Embodiments 1-57, wherein the average max load of the multilayered structure at about 23° C. under wet conditions is about 20-30 lbf.

Embodiment 59 provides the photobioreactor of any one of Embodiments 1-58, wherein the average max load of the multilayered structure at about 66° C. under dry conditions is about 5-70 lbf.

Embodiment 60 provides the photobioreactor of any one of Embodiments 1-59, wherein the average max load of the multilayered structure at about 66° C. under dry conditions is about 17-27 lbf.

Embodiment 61 provides the photobioreactor of any one of Embodiments 1-60, wherein the average max load of the multilayered structure at about 66° C. under wet conditions is about 5-70 lbf.

Embodiment 62 provides the photobioreactor of any one of Embodiments 1-61, wherein the average max load of the multilayered structure at about 66° C. under wet conditions is about 17-27 lbf.

Embodiment 63 provides the photobioreactor of any one of Embodiments 1-62, wherein the average 10% secant modulus of the multilayered structure at about 23° C. under dry conditions is about 5,000-150,000 psi.

Embodiment 64 provides the photobioreactor of any one of Embodiments 1-63, wherein the average 10% secant modulus of the multilayered structure at about 23° C. under dry conditions is about 73,000-93,000 psi.

Embodiment 65 provides the photobioreactor of any one of Embodiments 1-64, wherein the average 10% secant modulus of the multilayered structure at about 23° C. under wet conditions is about 5,000-150,000 psi.

Embodiment 66 provides the photobioreactor of any one of Embodiments 1-65, wherein the average 10% secant modulus of the multilayered structure at about 23° C. under wet conditions is about 92,000-112,000 psi.

Embodiment 67 provides the photobioreactor of any one of Embodiments 1-66, wherein the average 10% secant modulus of the multilayered structure at about 66° C. under dry conditions is about 5,000-150,000 psi.

Embodiment 68 provides the photobioreactor of any one of Embodiments 1-67, wherein the average 10% secant modulus of the multilayered structure at about 66° C. under dry conditions is about 32,000-52,000 psi.

Embodiment 69 provides the photobioreactor of any one of Embodiments 1-68, wherein the average 10% secant modulus of the multilayered structure at about 66° C. under wet conditions is about 5,000-150,000 psi.

Embodiment 70 provides the photobioreactor of any one of Embodiments 1-69, wherein the average 10% secant modulus of the multilayered structure at about 66° C. under wet conditions is about 40,000-60,000 psi.

Embodiment 71 provides the photobioreactor of any one of Embodiments 1-70, comprising a plurality of compartments.

Embodiment 72 provides the photobioreactor of any one of Embodiments 1-71, wherein the biomaterial comprises at least one of algae, microalgae, and cyanobacteria.

Embodiment 73 provides a method of making a compartment wall for a photobioreactor, the method comprising: extruding resin comprising at least one polyolefin, and a resin comprising at least one of a cyclic olefin copolymer and a cyclic olefin polymer, to form a multilayered structure comprising at least one first layer comprising at least one polyolefin; and at least one second layer comprising at least one of a cyclic olefin copolymer and a cyclic olefin polymer.

Embodiment 74 provides the method of Embodiment 73, wherein the extruding is at least one of cast sheet extrusion, cast film extrusion, blown sheet extrusion, and blown film extrusion.

Embodiment 75 provides a photobioreactor, comprising: at least one compartment comprising an interior and at least one wall, the interior adapted to hold a liquid and a phototrophic biological material, the wall being at least partially transparent and comprising a multilayered structure comprising a1) at least one first layer comprising at least one polyolefin; a2) at least one first layer comprising at least one polyolefin; a3) at least one first layer comprising at least one polyolefin; b1) at least one second layer comprising at least one of a cyclic olefin copolymer and a cyclic olefin polymer; b2) at least one second layer comprising at least one of a cyclic olefin copolymer and a cyclic olefin polymer; b3) at least one second layer comprising at least one of a cyclic olefin copolymer and a cyclic olefin polymer; c1) at least one first layer comprising at least one polyolefin; c2) at least one first layer comprising at least one polyolefin; and c3) at least one first layer comprising at least one polyolefin; wherein layer a1) is in contact with layer a2), layer a2) is in contact with layer a3), layer a3) is in contact with layer b1), layer b1) is in contact with layer b2), layer b2) is in contact with layer b3), layer b3) is in contact with layer c1), layer c1) is in contact with layer c2), and layer c2) is in contact with layer c3).

Embodiment 76 provides a multilayered structure comprising: a) at least one first layer comprising at least one polyolefin; b) at least one second layer comprising at least one of a cyclic olefin copolymer and a cyclic olefin polymer; and c) at least one first layer comprising at least one polyolefin; wherein the multilayered structure is at least partially transparent, layer a) is in contact with layer b), layer b) is in contact with layer c), and wherein at least one of layers a), b), and c) comprises more than one first or second layer.

Embodiment 77 provides the multilayered structure of Embodiment 76, comprising: a1) at least one first layer comprising at least one polyolefin; a2) at least one first layer comprising at least one polyolefin; b1) at least one second layer comprising at least one of a cyclic olefin copolymer and a cyclic olefin polymer; b2) at least one second layer comprising at least one of a cyclic olefin copolymer and a cyclic olefin polymer; c1) at least one first layer comprising at least one polyolefin; and c2) at least one first layer comprising at least one polyolefin; wherein layer a1) is in contact with layer a2), layer a2) is in contact with layer b1), layer b1) is in contact with layer b2), layer b2) is in contact with layer c1), and layer c1) is in contact with layer c2).

Embodiment 78 provides the multilayered structure of any one of Embodiments 76-77, comprising: a1) at least one first layer comprising at least one polyolefin; a2) at least one first layer comprising at least one polyolefin; a3) at least one first layer comprising at least one polyolefin; b1) at least one second layer comprising at least one of a cyclic olefin copolymer and a cyclic olefin polymer; b2) at least one second layer comprising at least one of a cyclic olefin copolymer and a cyclic olefin polymer; b3) at least one second layer comprising at least one of a cyclic olefin copolymer and a cyclic olefin polymer; c1) at least one first layer comprising at least one polyolefin; c2) at least one first layer comprising at least one polyolefin; and c3) at least one first layer comprising at least one polyolefin; wherein layer a1) is in contact with layer a2), layer a2) is in contact with layer a3), layer a3) is in contact with layer b1), layer b1) is in contact with layer b2), layer b2) is in contact with layer b3), layer b3) is in contact with layer c1), layer c1) is in contact with layer c2), and layer c2) is in contact with layer c3).

Embodiment 79 provides the apparatus or method of any one or any combination of Embodiments 1-78 optionally configured such that all elements or options recited are available to use or select from.

What is claimed is:

1. A multilayered structure, comprising:
at least one A layer (a2) comprising at least one polyolefin;
one A layer (a1) comprising at least one polyolefin;
at least one B layer (b1) comprising at least one of a cyclic olefin copolymer and a cyclic olefin polymer;
one A layer (c1) comprising at least one polyolefin; and
at least one A layer (c2) comprising at least one polyolefin;
wherein the multilayered structure is flexible and at least partially transparent, layer (a2) is fully in contact with layer (a1), layer (a1) is fully in contact with layer (b1), layer (b1) is fully in contact with layer (c1), and layer (c1) is fully in contact with layer (c2), and wherein the multilayered structure is free of tie layers between A layers and B layers;
wherein the multilayered structure has an average wall stress or hoop stress at failure that is higher than the average wall stress or hoop stress at failure of a corresponding multilayered structure having a poly(hexamethylene adipamide-co-caprolactam) layer in place of each of the B layers and having an anhydride-modified LLDPE tie layer in place of each of the at least one A layer (a1) and the at least one A layer (c1);
wherein the cyclic olefin copolymer or polymer of the B layer (b1) is independently a copolymer or polymer of a cyclic olefin having the structure (I)

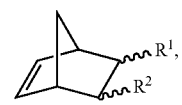

(I)

wherein
each carbon atom of structure (I) is independently unsubstituted or substituted with $R^3$;
$R^1$ and $R^2$ at each occurrence are each independently selected from H, J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, and $(C_1-C_{10})$heteroaryl$(C_1-C_{10})$alkyl, or wherein $R^1$ and $R^2$ together form structure (II)

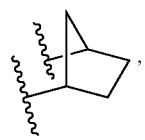

(II)

each carbon atom of structure (II) being independently unsubstituted or substituted with $R^3$;
$R^3$ at each occurrence is independently selected from J, $(C_1-C_{10})$alkyl, $(C_2-C_{10})$alkenyl, $(C_2-C_{10})$alkynyl, $(C_1-C_{10})$haloalkyl, $(C_1-C_{10})$alkoxy, $(C_1-C_{10})$haloalkoxy, $(C_1-C_{10})$cycloalkyl$(C_0-C_{10})$alkyl, $(C_1-C_{10})$heterocyclyl$(C_0-C_{10})$alkyl, $(C_1-C_{10})$aryl$(C_0-C_{10})$alkyl, and $(C_1-C_{10})$heteroaryl$(C_0-C_{10})$alkyl;
J at each occurrence is independently selected from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, C(O)$CH_2$C(O)R, C(S)R, C(O)OR, OC(O)R, OC(O)OR, C(O)N(R)$_2$, OC(O)N(R)$_2$, C(S)N(R)$_2$, (CH$_2$)$_{0-2}$NHC(O)R, N(R)N(R)C(O)R, N(R)N(R)C(O)OR, N(R)N(R)C(O)N(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(C(O)R)C(O)R, N(OR)R, C(=NH)N(R)$_2$, C(O)N(OR)R, and C(=NOR)R, wherein R at each occurrence is independently selected from the group consisting of hydrogen, (C$_1$-C$_{10}$)alkyl, (C$_1$-C$_{10}$)cycloalkyl, (C$_1$-C$_{10}$)cycloalkyl(C$_1$-C$_{10}$)alkyl, (C$_1$-C$_{10}$)aryl, (C$_1$-C$_{10}$)aralkyl, (C$_1$-C$_{10}$)heterocyclyl, (C$_1$-C$_{10}$)heterocyclyl(C$_1$-C$_{10}$)alkyl, (C$_1$-C$_{10}$)heteroaryl, and (C$_1$-C$_{10}$)heteroaryl(C$_1$-C$_{10}$)alkyl; and in R$^1$, R$^2$, and R$^3$, each alkyl, cycloalkyl, cycloalkylalkyl, aryl, aralkyl, heterocyclyl, heterocyclylalkyl, heteroaryl, heteroarylalkyl, is independently' unsubstituted or substituted with 1-3 J.

2. The multilayered structure of claim 1, comprising:
at least two or three of the B layers, wherein at least two of the at least two or three B layers are fully in contact with one another, and wherein the at least two or three B layers are between the at least two A layers.

3. The multilayered structure of claim 1, wherein the at least one B layer (b1) comprises:
at least one B layer (b1a); and
at least one B layer (b1b);
wherein layer (a2) is fully in contact with layer (a1), layer (a1) is fully in contact with layer (b1a), layer (b1a) is fully in contact with layer (b1b)), layer (b1b) is fully in contact with layer (c1), and layer (c1) is fully in contact with layer (c2).

4. The multilayered structure of claim 1, wherein the at least one A layer (a2) comprises
at least one A layer (a2a); and
at least one A layer (a2b);
the at least one B layer (b1) comprises
at least one B layer (b1a);
at least one B layer (b1b); and
at least one B layer (b1c);
the at least one A layer (c2) comprises
at least one A layer (c2a); and
at least one A layer (c2b);
wherein layer (a2a) is fully in contact with layer (a2b), layer (a2b) is fully in contact with layer (a1), layer (a1) is fully in contact with layer (b1a), layer (b1a) is fully in contact with layer (b1b), layer (b1b) is fully in contact with layer (b1c), layer (b1c) is fully in contact with layer (c1), layer (c1) is fully in contact with layer (c2a), and layer (c2a) is fully in contact with layer (c2b).

5. The multilayered structure of claim 1, wherein the total thickness of all of the A layers and all of the B layers is about 1-30 mils.

6. The multilayered structure of claim 1, wherein at least one A layer comprises at least one of ultra high molecular weight polyethylene (UHMWPE), high-density polyethylene (HDPE), cross-linked polyethylene (PEX or XLPE), medium density polyethylene (MDPE), linear low-density polyethylene (LLDPE), low-density polyethylene (LDPE), very low-density polyethylene (VLDPE), and a copolymer thereof.

7. The multilayered structure of claim 1, wherein at least one A layer comprises a polymer or copolymer of at least one of propene, butene, pentene, heptene, hexene, octene, nonene, decene, ethylene, a (C$_1$-C$_{10}$)alkylenoic acid, a vinyl (C$_1$-C$_{10}$)alkanoate ester, and a (C$_1$-C$_{10}$)alkyl (C$_1$-C$_{10}$)alkylenoate ester.

8. The multilayered structure of claim 1, wherein at least one layer comprises a polymer or copolymer of at least one cyclic olefin selected from 8,9,10-trinorborn-2-ene ("norbornene"), 8,9,10-trinorborn-2-ene substituted at at least one of the 5- and 6-position independently with R$^3$, 1,2,3,4,4a,5,8,8a-octahydro-1,4:5,8-dimethanonaphthalene ("tetracyclododecene"), and 1,2,3,4,4a,5,8,8a-octahydro-1,4:5,8-dimethanonaphthalene substituted at at least one of the 2- or 3-position with R$^3$, wherein R$^3$ at each occurrence is independently selected from methyl, ethyl, propyl, butyl, and pentyl, wherein R$^3$ is branched or unbranched.

9. The multilayered structure of claim 1, wherein at least one B layer comprises a copolymer of a cyclic olefin and at least one of ethylene, propene, butene, pentene, heptene, hexene, octene, nonene, decene, a (C$_1$-C$_{10}$)alkylenoic acid, a vinyl (C$_1$-C$_{10}$)alkanoate ester, and a (C$_1$-C$_{10}$)alkyl (C$_1$-C$_{10}$) alkylenoate ester.

10. The multilayered structure of claim 1, wherein the multilayered structure is extruded using at least one of cast sheet extrusion, cast film extrusion, blown sheet extrusion, and blown film extrusion.

11. The multilayered structure of claim 1, wherein the average pressure at failure of the multilayered structure is about 10-100 psi.

12. The multilayered structure of claim 1, wherein the average stress at failure of the multilayered structure is about 250-3000 psi.

13. The multilayered structure of claim 1, wherein the average % elongation of the multilayered structure at about 23° C. under wet conditions is about 300-2500%.

14. The multilayered structure of claim 1, wherein the average max load of the multilayered structure at about 23° C. under wet conditions is about 5-70 lbf.

15. The multilayered structure of claim 1, wherein the average max load of the multilayered structure at about 23° C. under wet conditions is about 20-30 lbf.

16. The multilayered structure of claim 1, wherein the average 10% secant modulus of the multilayered structure at about 23° C. under wet conditions is about 5,000-150,000 psi.

17. A multilayered structure, comprising:
at least one A layer (a3) comprising at least one polyolefin;
at least one A layer (a2) comprising at least one polyolefin;
one A layer (a1) comprising at least one polyolefin;
at least one B layer (b1) comprising at least one of a cyclic olefin copolymer and a cyclic olefin polymer;
at least one B layer (b2) comprising at least one of a cyclic in copolymer and a cyclic olefin polymer;
at least one B layer (b3) comprising at least one of a cyclic olefin copolymer and a cyclic olefin polymer;
one A layer (c1) comprising at least one polyolefin;
at least one A layer (c2) comprising at least one polyolefin; and
at least one A layer (c3) comprising at least one polyolefin;
wherein the multilayered structure is flexible and at least partially transparent, wherein layer (a3) is fully in contact with layer (a2), layer (a2) is fully in contact with layer (a1), layer (a1) is fully in contact with layer (b1), layer (b1) is fully in contact with layer (b2), layer (b2) is fully in contact with layer (b3), layer (b3) is fully in contact with layer (c1), layer (c1) is fully in contact with layer (c2), layer (c2) is fully in contact with layer (c3), and wherein the multilayered structure is free of tie layers between A layers and B layers;
wherein the cyclic olefin copolymer or polymer of B layers (b1), (b2), and (b3) is independently a copolymer or polymer of a cyclic olefin having the structure (I)

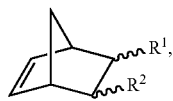

(I)

wherein
each carbon atom of structure (I) is independently unsubstituted or substituted with $R^3$;
$R^1$ and $R^2$ at each occurrence are each independently selected from H, J, $(C_1\text{-}C_{10})$alkyl, $(C_2\text{-}C_{10})$alkenyl, $(C_2\text{-}C_{10})$alkynyl, $(C_1\text{-}C_{10})$haloalkyl, $(C_1\text{-}C_{10})$alkoxy, $(C_1\text{-}C_{10})$haloalkoxy, $(C_1\text{-}C_{10})$cycloalkyl$(C_0\text{-}C_{10})$alkyl, $(C_1\text{-}C_{10})$heterocyclyl$(C_0\text{-}C_{10})$alkyl, $(C_1\text{-}C_{10})$aryl$(C_0\text{-}C_{10})$alkyl, and $(C_1\text{-}C_{10})$heteroaryl$(C_0\text{-}C_{10})$alkyl, or wherein $R^1$ and $R^2$ together form structure (II)

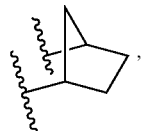

(II)

each carbon atom of structure (II) being independently unsubstituted or substituted with $R^3$;
$R^3$ at each occurrence is independently selected from J, $(C_1\text{-}C_{10})$alkyl, $(C_2\text{-}C_{10})$alkenyl, $(C_2\text{-}C_{10})$alkynyl, $(C_1\text{-}C_{10})$haloalkyl, $(C_1\text{-}C_{10})$alkoxy, $(C_1\text{-}C_{10})$haloalkoxy, $(C_1\text{-}C_{10})$cycloalkyl$(C_0\text{-}C_{10})$alkyl, $(C_1\text{-}C_{10})$heterocycyl$(C_0\text{-}C_{10})$alkyl, $(C_1\text{-}C_{10})$aryl$(C_0\text{-}C_{10})$alkyl, and $(C_1\text{-}C_{10})$heteroaryl$(C_0\text{-}C_{10})$alkyl;
J at each occurrence is independently selected from F, Cl, Br, I, OR, CN, $CF_3$, $OCF_3$, R, O, S, C(O), S(O), methylenedioxy, ethylenedioxy, $N(R)_2$, SR, S(O)R, $SO_2R$, $SO_2N(R)_2$, $SO_3R$, C(O)R, C(O)C(O)R, $C(O)CH_2C(O)R$, C(S)R, C(O)OR, OC(O)R, OC(O)OR, $C(O)N(R)_2$, $OC(O)N(R)_2$, $C(S)N(R)_2$, $(CH_2)_{0-2}NHC(O)R$, N(R)N(R)C(O)R, N(R)N(R)C(O)OR, $N(R)N(R)C(O)N(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(C(O)R)C(O)R, N(OR)R, $C(=NH)N(R)_2$, C(O)N(OR)R, and C(=NOR)R, wherein R at each occurrence is independently selected from the group consisting of hydrogen, $(C_1\text{-}C_{10})$alkyl, $(C_1\text{-}C_{10})$cycloalkyl, $(C_1\text{-}C_{10})$cycloalkyl$(C_1\text{-}C_{10})$alkyl, $(C_1\text{-}C_{10})$aryl, $(C_1\text{-}C_{10})$aralkyl, $(C_1\text{-}C_{10})$heterocyclyl, $(C_1\text{-}C_{10})$heterocyclyl$(C_1\text{-}C_{10})$alkyl, $(C_1\text{-}C_{10})$heteroaryl, and $(C_1\text{-}C_{10})$heteroaryl$(C_1\text{-}C_{10})$alkyl; and
in $R^1$, $R^2$, and $R^3$, each alkyl, cycloalkyl, cycloalkylalkyl, aryl, aralkyl, heterocyclyl, heterocyclylalkyl, heteroaryl, heteroarylalkyl, is independently unsubstituted or substituted with 1-3 J.

18. A multilayered structure comprising:
at least one A layer (a2) comprising at least one polyolefin;
one A layer (a1) comprising at least one polyolefin;
at least one B layer (b1) comprising at least one of a cyclic olefin copolymer and a cyclic olefin polymer;
one A layer (c1) comprising at least one polyolefin; and
at least one A layer (c2) comprising at least one polyolefin;
wherein the multilayered structure is flexible and at least partially transparent, layer (a2) is fully in contact with layer (a1), layer (a1) is fully in contact with layer (b1), layer (b1) is fully in contact with layer (c1), and layer (c1) is fully in contact with layer (c2), wherein the multilayered structure is free of tie layers between A layers and B layers;
wherein the multilayered structure has an average wall stress or hoop stress at failure that is higher than the average wall stress or hoop stress at failure of a corresponding multilayered structure having a poly(hexamethylene adipamide-co-caprolactam) layer in place of each of the B layers and having an anhydride-modified LLDPE tie layer in place of each of the at least one A layer (a1) and the at least one A layer (c1); and
wherein the cyclic olefin copolymer or polymer of the B layer (b1) is a copolymer or polymer of a cyclic olefin having the structure:

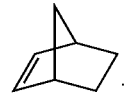

* * * * *